US008282943B2

(12) United States Patent
Jochem et al.

(10) Patent No.: US 8,282,943 B2
(45) Date of Patent: Oct. 9, 2012

(54) THERAPEUTIC COMPOSITION FOR USE IN THE PREVENTION AND TREATMENT OF BONE METASTASES

(76) Inventors: Ralf Jochem, Bad Homburg (DE); Franz Paul Armbruster, Bobenheim-Roxheim (DE); Veit Braun, Mainz (DE); Christoph Von Eichel-Streiber, Schweppenhausen (DE)

( * ) Notice: Subject to any disclaimer, the term of this patent is extended or adjusted under 35 U.S.C. 154(b) by 833 days.

(21) Appl. No.: 11/921,421

(22) PCT Filed: May 31, 2006

(86) PCT No.: PCT/EP2006/005191
§ 371 (c)(1), (2), (4) Date: Jan. 30, 2009

(87) PCT Pub. No.: WO2006/128689
PCT Pub. Date: Dec. 7, 2006

(65) Prior Publication Data
US 2009/0142372 A1 Jun. 4, 2009

(30) Foreign Application Priority Data

May 31, 2005 (DE) ......................... 10 2005 024 836
Feb. 1, 2006 (DE) ......................... 10 2006 004 612

(51) Int. Cl.
*A61K 39/385* (2006.01)
*A01N 63/02* (2006.01)

(52) U.S. Cl. ................. 424/277.1; 424/93.4; 424/93.41; 424/93.42; 424/93.46; 424/93.462; 424/93.6

(58) Field of Classification Search ........................ None
See application file for complete search history.

(56) References Cited

U.S. PATENT DOCUMENTS 7,825,219 B2 * 11/2010 Armbruster et al. ....... 530/387.1

FOREIGN PATENT DOCUMENTS

WO WO-02/100899 A2 12/2002
WO WO-02/100901 A2 12/2002

OTHER PUBLICATIONS

Cheadle & Jackson (Immunology, 2002, vol. 107, pp. 10-19).*
Tobias Baeuerle, et al., "Characterization of a rat model with site-specific bone metastasis induced by MDA-MB-231 breast cancer cells and its application to the effects of an antibody against bone sialoprotein," Int. J. Cancer, vol. 115, pp. 177-186 (2005).
Gabri van der Pluijm, et al., "Bone Sialoprotein Peptides Are Potent Inhibitors of Breast Cancer Cell Adhesion to Bone," Cancer Research, vol. 56, pp. 1948-1955 (1996).
Tobias Bauerle, et al., "Treatment of bone metastasis induced by MDA-MB-231 breast cancer cells with an antibody against bone sialoprotein," International Journal of Oncology, vol. 28, pp. 573-583 (2006).
Stephane Mesnage, et al., "Cell Surface-Exposed Tetanus Toxin Fragment C Produced by Recombinant *Bacillus anthracis* Protects against Tetanus Toxin," Infection and Immunity, vol. 67, No. 9, pp. 4847-4850 (1999).
Christophe D Reymond, et al., "Anchoring of an Immunogenic *Plasmodium falciparum* circumsporozoite Protein on the Surface of *Dictyostelium discoideum*," Journal of Biological Chemistry, vol. 270, No. 21, pp. 12941-12947 (1995).
George Georgiou, et al., "Display of heterologous proteins on the surface of microorganisms: From the screening of combinatorial libraries to live recombinant vaccines," Nature Biotechnology, vol. 15, pp. 29-33 (1997).
Francois Cano, et al., "A surface-displayed cholera toxin B peptide improves antibody responses using food-grade staphylococci for mucosal subunit vaccine delivery," Fems Immunology and Medical Microbiology, vol. 25, pp. 289-298 (1999).
Naima G. Cortes-Perez, et al., "Mice immunization with live lactococci displaying a surface anchored HPV-16 E7 oncoprotein," Fems Microbiology Letters, vol. 229, pp. 37-42 (2003).
Sissela Liljeqvist, et al., "Surface Display of the Cholera toxin B Subunit on *Staphylococcus xylosus* and *Staphylococcus carnosus*," Applied and Environmental Microbiology, vol. 63, No. 7, pp. 2481-2488 (1997).
Ivaylo Gentschev, et al., "The *E. coli* α-hemolysin secretion system and its use in vaccine development," Trends in Microbiology, vol. 10, No. 1, pp. 39-45 (2002).
Kees Leenhouts, et al., "Anchoring of proteins to lactic acid bacteria," Antonie Van Leeuwenhoek, vol. 76, pp. 367-376 (1999).

* cited by examiner

*Primary Examiner* — Karen Canella
(74) *Attorney, Agent, or Firm* — Birch, Stewart, Kolasch & Birch, LLP

(57) ABSTRACT

The invention is relates to drugs on the basis of antibodies against non-cellular bone matrix proteins, especially BSP, for use in the prevention and treatment of bone metastases. According to the invention, the antibodies are induced in the patient by recombinantly expressing antigenic determinants of bone matrix proteins in *Listeria* and anchoring them on the surfaces thereof. The antigenic determinants are selected according to whether they are characteristic of antigens that are expressed by the tumor cells themselves.

16 Claims, 9 Drawing Sheets

FIG. 1

```
┌─────────────────────────────────────────────┐
│   Analysis of BSP structure for tumourgenic │
│   mutations and choice of tumour BSP        │
│   fragments for anchoring on listeria       │
└─────────────────────────────────────────────┘
                      │
                      ▼
┌─────────────────────────────────────────────┐
│      Functional anchoring of tumour         │
│         BSP fragments on listeria           │
└─────────────────────────────────────────────┘
                      │
                      ▼
┌─────────────────────────────────────────────┐
│  Choice of secretion signals for the        │
│  presentation of tumour BSP epitopes on     │
│  listeria                                   │
└─────────────────────────────────────────────┘
                      │
                      ▼
┌─────────────────────────────────────────────┐
│  Choice of conditions for a stable          │
│  anchoring and presentation of tumour BSP   │
│  epitopes on listeria                       │
└─────────────────────────────────────────────┘
                      │
                      ▼
┌─────────────────────────────────────────────┐
│       Production of vaccination bacteria    │
└─────────────────────────────────────────────┘
                      │
                      ▼
┌─────────────────────────────────────────────┐
│  Immunisation of patients, which have bone  │
│  metastases or tumourgenic BSP expression   │
└─────────────────────────────────────────────┘
```

Anchoring of vBSP-2

Anchoring vectors

THERAPEUTIC COMPOSITION FOR USE IN THE PREVENTION AND TREATMENT OF BONE METASTASES

FIELD OF THE INVENTION

The invention relates to medicaments for use in the prevention and treatment of bone metastases which are based on antibodies against non-cellular bone matrix proteins.

BACKGROUND OF THE INVENTION

A primary cancer is often followed by secondary bone tumors. Despite all medical advances, bone tumors cannot be healed as they generally occur spread-out and can hardly be treated surgically. The probability of bone metastases is larger than 96% in the case of multiple myeloma, between 65% and 75% in the case of cancers of the breast and prostate, and between 30% and 50% in the case of cancers of the lung, kidney, cervix and bladder. Systemic chemotherapies have hardly any effect. Initial successes have been achieved using therapeutic antibodies. However, when therapeutic antibodies are used, there is the problem that they are mostly directed against targets which are only present on proliferating tumor cells. Generally not detectable are non-proliferating tumor cells in the blood circulation and latent metastases.

There is a close relationship between the occurrence of the bone matrix proteins osteopontin (OPN), osteonectin (ON) and bone-sialoprotein II (BSP) in the primary tumor on one hand, and the later occurrence of secondary blastomas of the bones on the other hand. The cells of an osteotropic metastasizing primary tumor nearly always express significant amounts of BSP or OPN (I. J. Diel et al., Clinic Cancer Res, 1999, 5:3914; A. B. Tuck et al., J Mammary Gland Biol Neplasia, 2001, 6:419; P. S. Rudland et al., Cancer Res 2002, 62:3417; D. Agrawal et al., J Natl Cancer Inst, 2002, 94:513; D. Waltregny et al., J Bone Miner Res, 2000, 15(5):834; A. Bellahcène et al., J Bone Miner Res, 1996, 11:665; D. Waltregny et al., J Nat Cancer Inst, 1998, 90:1000; A. Bellahcène et al., Int. J. Cancer, 1996, 69:350; WO 02/100901 (Immundiagnostik AG), WO 02/25285 (Smith et al.)).

BSP is a phosphorylated glycoprotein with a relative mass of about 80 kDa in SDS-PAGE. The cDNA for BSP codes for a peptide sequence of about 33 kDa (L. W. Fischer et al., J Biol Chem, 1990, 265:2347; U.S. Pat. No. 5,340,934 (Termine)). It represents about 10% to 15% of the non-collagen proteins in the bone matrix, and it is normally expressed by cells that are involved in the formation of dentine, bone and cartilage, such as osteoblasts, developing osteocytes, hypertrophic chondrocytes, odontoblasts and cementoblasts. As an adhesion molecule, BSP supports the attachment and spreading of osteoblasts and osteoclasts on the bone tissue matrix. The switching-off of the BSP-gene in knock-out mice did, however, not lead to a visible disruption of skeleton formation. However, BSP has been attributed a role in bone microcalcification and bone colony formation of tumor cells (V. Castronovo et al., Int J Oncol, 1998, 12:308; A. Bellahcène et al., Int J Cancer, 1996, 69:350).

Free BSP is bound with high affinity by complement factor H in body fluids. There are many antibodies against BSP peptide structures, recombinant BSP and BSP isolated from bone, which do not recognise and bind BSP in serum (L. W. Fisher et al., Acta Orthop Scand Suppl 1995, 266:61; J. T. Stubbs (III) et al. J Bone Miner Res, 1997, 12(8):1210). The 150 kDa large factor H molecule most likely encloses the BSP molecule in such a way that these antibodies cannot bind. Trophoblasts and BSP producing tumor cells are therefore also protected from an attack by the immune system (N. S. Fedarko et al. J. Biol. Chem., 2000, 275, 16666-16672; WO 00/062065). The heavy glycosylation of BSP may also play a role in this observation. Furthermore, BSP may bind through its RGD sequence (arginine-glycine-aspartic acid) to alpha (v)beta(3) integrin receptors on the cell wall. Thus, BSP is further involved in the adhesion, dissemination and orientation of the endothelial cells and the angiogenesis around a tumor (A. Bellahcène et al. Circ Res. 2000, 86(8):885-91). These properties make BSP, alongside OPN and ON in the family of non-collagen integrin receptor binding glycoproteins, a starting point for medicaments of all kinds (U.S. Pat. No. 5,780,526; U.S. Pat. No. 5,767,071; U.S. Pat. No. 5,792,745; U.S. Pat. No. 5,989,383; U.S. Pat. No. 5,773,412; U.S. Pat. No. 5,849,865).

There have been attempts to inhibit through RGD-antagonists the binding of BSP to the vitronectin and integrin receptors of the tumor and endothelial cells (U.S. Pat. No. 6,069,158; U.S. Pat. No. 6,008,213; U.S. Pat. No. 5,849,865; van der Pluijm et al., Cancer Res., 1996, 56, 1948-1955). EP 1 084 719 (DePuy Orthopaedics Inc.) describes BSP an active agent for supporting the repair of damaged bone and connective tissues. WO 94/11310 (Alfa-Laval Agriculture Intern. AB) discloses a BSP-binding protein from *Staphylococcus aureus* for a treatment of infections and inflammatory diseases of the bone. WO 02/100899 (Armbruster Biotechnology GmbH) discloses an active ingredient against bone metastases based on antibodies against BSP. WO 00/36919 (Univ. Virginia Patent Found.) describes regulatory elements for control and inhibition of BSP expression in tumor cells and connective tissue cells. Finally, EP 0 020 789 (DKFZ) discloses an inhibition of cell migration and bone metastasis formation by antisense-oligonucleotides (quod vide Adwan-Hassan et al. in Cancer Gene Therapy, 2003:1; Intern J Oncol, 2004, 24:1235-1244; Proc Am Assoc Cancer Res Ann, 2003, 44:56). WO 2006/036550 (Trustees of the Univ. of Pennsylvania; published after the priority date of this application) further describes vaccines on the basis of *Listerium* and fusion proteins of listeriolysin and CD8+-T-cell epitopes (Her-2) for a treatment of osteotropic tumors and carcinoma.

Therefore, it has been examined what causes a primary tumor, which can normally be surgically removed, to produce metastases and how bone metastases may be prevented and what is needed for their treatment or eventual cure. In previous attempts, it proved disadvantageous that a therapy based on antisense oligonucleotides or antibodies, when effective at all, can only be maintained effective for a limited period. There is not only a problem of dose and application, but also due to the development of autoantibodies against the therapeutic immunoglobulins and regulatory nucleotides. One should further not forget that the body contains natural endogenous BSP so that an immune reaction against endogenous BSP is inhibited. On the other hand, prophylaxis or a direct treatment of bone metastases must be carried on over very long periods in order to be potentially successful. The danger of an occurrence of bone metastases will last for decades after a treatment of a primary osteotropic tumor. Thus, there is a need for a therapeutic composition that sustainably prevents a colony forming and development of bone tumors, and fights any existing bone metastases.

SUMMARY OF THE INVENTION

The problem is solved by a therapeutic composition in accordance with claim 1. Preferred embodiments of the invention are described in the dependent claims.

According to the invention, the pharmaceutical composition for treatment and prophylaxis of bone tumors and metastases that preferably colonize into bone tissue contains as active ingredient dead or weakly pathogenic micro-organisms, which contain a gene for antigenic fragments of the bone sialoprotein and express one or more bone sialoprotein antigens that differ in at least one structural feature from endogenous bone sialoprotein of normal osteoblasts so that their administration produces an immune reaction against the altered bone sialoprotein. The expressed bone sialoprotein molecules preferably possess structural features of a bone sialoprotein that is specifically expressed by the osteotropic cells of a primary tumor. According to the invention, the microorganism is selected from bacteria, viruses and monads, preferably from Gram-positive bacteria such as *Listeria*. It may also be selected from the species *Aeromonas, Bartonella, Bruceila, Bacilli, Bacillus subtilis, Lactobacilli, Pseudomonades, Staphylococci, Yersinia, Campylobacter, Clostridia, Enterobacteriaceae, Legionella*, preferably *Listeria*, more preferably *Listeria monocytogenes, Mycobacterium, Rhenibacterium, Rhodococcus*, bacteria of the species *Yersinia, Escherichia, Shigella, Salmonella*, and bacteria, which may survive in a eukaryotic host organism. Particularly preferred is an embodiment where the microorganism carries one or more BSP antigen determinants anchored to its surface, more particularly, tumor-typical bone sialoprotein or fragments thereof. The microorganism may carry anchored to its surface an underglycosylated bone sialoprotein antigen or fragments thereof. For high therapeutic activity, it is important that the bone sialoprotein antigen possesses an epitope, which, when in a complex of BSP and complement factor H, is free for the binding of an antibody. According to the invention, such a bone sialoprotein antigen contains one or more copies of the following amino acid sequences:

```
YTGLAAIQLPKKAGD         SEQ. ID NO. 5

TGLAA                   SEQ. ID NO. 3

YTGLAA                  SEQ. ID NO. 4

YESENGEPRGDNYRAYED      SEQ. ID NO. 6

LKRFPVQGG               SEQ. ID NO. 7

EDATPGTGYTGLAAIQLPKKAG  SEQ. ID NO. 10
```

In one embodiment of the invention, the pharmaceutical composition comprises as an active ingredient an immunogen with a hapten, which is present on bone sialoprotein from tumor cells, and more preferably the antigen determinant of bone sialoprotein in at least two or more copies. The pharmaceutical composition of the invention can be used for a treatment of tumors selected from the group comprising tumors of the prostate, breast, lung, kidney and thyroid, tumors of the circulatory system, lymphoid system, cardio-vascular system, neurological system, respiratory tract, intestinal tract, endocrine system, skin including adnexa, musculoskeletal system and urogenital system, including the kidneys.

A further aspect of the invention relates to a method for developing a therapeutically active composition comprising the of steps: (i) selecting a protein relevant for a disease; (ii) cloning and expression of an antigenic structure of the relevant protein in a microorganism, which expresses, secretes and presents an antigenic fragment thereof, anchored to the membrane, on its cell surface; (iii) eliciting of antibodies against the antigenic fragment of the disease-relevant protein; (iv) testing of the antibodies for therapeutic activity. Preferably, the microorganism is a Gram-positive bacterium, more preferably, the microorganism is *Listerium*. In the process, sera of mammals are used to screen the antigens, and the sera are then examined for the presence antibodies against the antigenic fragment. For the purpose of this invention, disease-relevant proteins are examined, which have a physiological function in the colonialization of tumor cells into bones, for example, the extracellular bone matrix proteins bone sialoprotein (BSP), osteopontin (OPN), osteonectin (ON) and growth factors for osteotropic tumors. The invention also incorporates therapeutically useful antibodies and vaccines obtained by this process.

Another aspect of the invention concerns a process for treatment and prevention of bone tumors and metastases, which preferably settle into bone tissue, including the administration of dead or weakly pathogenic microorganisms, which possess one or more antigens of the bone sialoprotein anchored on the surface, which differ in at least one structural feature from endogenous bone sialoprotein of normal osteoblasts, so that their administration elicits an immune reaction, which is directed against the tumor and its disseminating tumor cells. In an alternative process comprising the administration of peptidic molecules or carrier proteins with antigenic determinants of the bone sialoprotein, which are characteristic for a bone sialoprotein produced by tumor cells, so that an immune reaction is elicited against the tumor and its disseminating tumor cells. A further embodiment of the process comprises the administration of peptidic molecules or carrier proteins with antigenic determinants of bone sialoprotein, which are characteristic for a bone sialoprotein from tumor cells so that an immune reaction is elicited which acts against the tumor and its spreading tumor cells. It is preferred in this connection when the antigenic determinants occur several times on the peptidic molecules or carrier proteins or when the peptidic molecules are coupled to beta-alanine.

In accordance with the invention, the therapeutic composition for treatment and prophylaxis of bone tumors and metastases which preferably settle into bone tissue contains as active agent dead or weakly pathogenic microorganisms, which contain a gene for BSP leading to an expression of one or more BSP molecules, which differ in at least one structural feature from endogenous BSP of normal osteoblasts, so that, when administered, an immune reaction against the modified BSP is induced. It is preferred that the expressed BSP molecules possess structural features characteristic for the tumor form, such as can be found with BSP from the osteotropic cells of a primary tumor. The respective microorganism is selected from bacteria, viruses and monads, and is preferably a Gram-positive bacterium, most preferably *Listerium*. The microorganism may be selected from bacteria propagating intracellularly in host cells, for example from the species *Aeromonas, Bartonella, Bruceila, Bacilli, Bacillus subtilis, Lactobacilli, Pseudomonades, Staphylococci, Campylobacter, Clostridia, Enterobacteriaceae, Legionella, Listeria, Mycobacterium, Rhenibacterium, Rhodococcus, Yersinia, Escherichia, Shigella, Salmonella*, and bacteria, which may survive in an eukaryotic host organism, such as *Listeria*. Bacteria normally not propagating intracellularly may further be implemented through genetic manipulations with factors that allow them to access cells. Advantageously, the genetically manipulated microorganism contains an exogenous or heterologous suicide gene and can produce a targeted somatic transgenic modification in the host cells. Particularly preferred is the use of *Listeria* for the production of a therapeutic composition in accordance with the invention.

A further aspect of the invention concerns a therapeutic composition, wherein the genetically modified microorganism, for example *Listerium*, has anchored on its surface a BSP antigen, respectively, an antigenic determinant of BSP, preferably originating from human BSP and fragments thereof, most preferably from glycosylation-deficient BSP and fragments thereof. The expressed BSP fragments will then be recognized as foreign in a mammal, particular, when located on the membrane of a microorganism and on the cell surface of infected host cells, respectively. The so elicited autoantibodies then bind to the BSP antigen of osteotropic tumor cells. An analogous effect may be achieved by coupling amino acids characteristic for bacteria such as beta-alanine (3-aminopropionic acid) with the peptidic antigenic determinants of BSP at the C-terminal end or the N-terminal end of the peptide or both. An immunogenic BSP and, respectively, a tumor BSP isoform determinant may be produced hereby which may be used as a vaccine against BSP.

Preferred DNAs for producing specific anti-tumor-BSP antibodies encode amongst others the following sequences of human bone sialoprotein (SWISSPROT: SIAL_HUMAN, Acc. No. P21815) and its homologues:

```
                                             SEQ ID NO: 1
X-YTGLAAIQLPKKAGD-Z

SEQ ID NO: 2
X-FSMKNLHRRVKIEDSEENGVFKYRPRYYLYKHAYFYPHLKRFPVQGSS

DSSEENGDDSSEEEEEEETSNEGENNEESNEDEDSEAENTTLSATTLGY

GEDATPGTGYTGLAAIQLPKKAGDITNKATKEKESDEEEEEEEGNENEE

SEAEVDENEQGINGTSTNSTEAENGNGSSGVDNGEEGEEESVTGANAEGT

TETGGQGKGTSKTTTSPNGGFEPTTPPQVYRTTSPPFGKTTTVEYEGEYE

YTYDNGYEIYESENGEPRGDNYRAYEGEYSYFKGQGYDGYDGQNYYH

HQ-Z
```

The highlighted threonine is not or incompletely or differently glycosylated in the BSP tumor isoform. In one embodiment, this threonine is converted into an amino acid which can not be glycosylated. X and Z represent amino acid residues and/or peptide moieties, for example, a membrane anchor, poly(histidine), poly(His)$_{5-12}$, or beta-alanine. SEQ ID NO: 2 may be modified as follows: Position 179 Gly→Val; Position 252 Val→Ala, Position 254 Glu→Asp; Position 279 Asp→Gly.

In one embodiment of the invention the therapeutic composition brings about the formation of endogenous antibodies against a BSP, which posttranslational glycosylation is modified or incomplete in the region of amino acids 120 to 135 (SWISSPROT: SIAL_HUMAN, Acc. No. P21815) compared to regular BSP from bones.

Preferred is the induction of endogenous autoantibodies which recognize a hBSP-epitope comprising the amino acid sequence TGLAA (SEQ ID NO: 3) or YTGLAA (SEQ ID NO: 4), and optionally sugar groups and a carrier molecule.

Hence, the vaccine of the invention gives rise to endogenous autoantibodies against a BSP tumor isoform. The so induced immunity therefore protects against a docking of metastasizing osteotropic tumor cells to bone tissue and results in a cell-mediated cytotoxicity against cells producing the tumor isoform of BSP.

Another aspect of the invention concerns a composition, wherein the BSP antigen contains an antigenic determinant, respectively an epitope, which is free for the binding of an antibody even when in a complex of complement factor H and BSP. The antigenic determinant of BSP may contain one or more copies of the following amino acid sequences:

```
TGLAA                    SEQ ID NO: 3

YTGLAA                   SEQ ID NO: 4

YTGLAAIQLPKKAGD          SEQ ID NO: 5

YESENGEPRGDNYRAYED       SEQ ID NO: 6

LKRFPVQGG                SEQ ID NO: 7
```

A preferred goal is hereby a therapeutic composition wherein the active ingredient possesses a hapten that is also present on BSP from tumor cells. The composition of the invention can be used for a treatment of tumors and carcinoma selected from a group comprising tumors of the prostate, breast, lung, kidneys and thyroid, tumors of the circulatory system, lymphoid system, cardiovascular system, neurological system, respiratory tract, digestive tract, endocrinal system, skin including adnexa, musculoskeletal system and urogenital system, including the kidneys.

A further aspect of the invention relates to a process for the development of an active composition, or of a vaccine, comprising the following steps: (i) selecting a protein relevant for the disease; (ii) cloning and expression of an antigenic structure of the relevant protein in a microorganism, which expresses, secretes and presents on the cell surface, anchored to the cell membrane, the antigenic structure; (iii) eliciting of antibodies against the antigenic structure of the disease-relevant protein; (iv) testing of the antibodies for therapeutic activity and use of the antibodies in a therapeutic composition, for example in a vaccine. The microorganism that presents the antigenic structure on its surface may be a Gram-positive bacterium, preferably *Listerium*. Preferred microorganisms induce a somatic transgenicity in host cells and they present the antigenic structure, inclusive posttranslational modifications, on the surface of the host cells. Particularly preferred are microorganisms such as *Listerium*, which are able to break the immunotolerance against an antigen expressing tumor. This may be achieved in particular by anchoring and presenting the antigen on the surface of the microorganism, or by coupling the antigen with bacteria characteristic amino acids such as beta-alanine. The microorganism may be inactivated prior to step (iii). It is further contemplated to test sera of mammalians for the presence of antibodies against the antigenic structure of the disease-relevant protein, and in particular to examine the proteins which have a physiological function in the settling of tumor cells in bones. The most promising proteins in this connection are mainly the extracellular bone matrix proteins bone sialoprotein (BSP), osteopontin (OPN), osteonectin (ON) and the growth factors for tumors. The process of the invention may be broadly applied as a screening process. In this case a multitude of antigenic structures of disease-relevant proteins are cloned in microorganisms, expressed and anchored on the surface, and mammalian sera screened for antibodies against the antigenic fragments, in order to select for therapeutically useful antigenic determinants, fragments and haptens, as well as antibodies. The anamnesis of these mammals, respectively patients, especially of the ones with spontaneous recovery, then points to a possible activity of the antibodies. This results in therapeutically active antibodies and microorganisms having the antigenic structure on the surface, and finally vaccines on basis thereof.

Further aspects and advantages of the invention are described in the detailed description of the invention and by attached figures and examples.

BRIEF DESCRIPTION OF THE FIGURES

FIG. 1 shows a block diagram of the process of the invention for the production of bacteria having antigen determinants from BSP, which elicit an immune reaction against osteotropic tumor cells and the settling of tumor cells in bones;

DETAILED DESCRIPTION OF THE INVENTION

Figure 2:
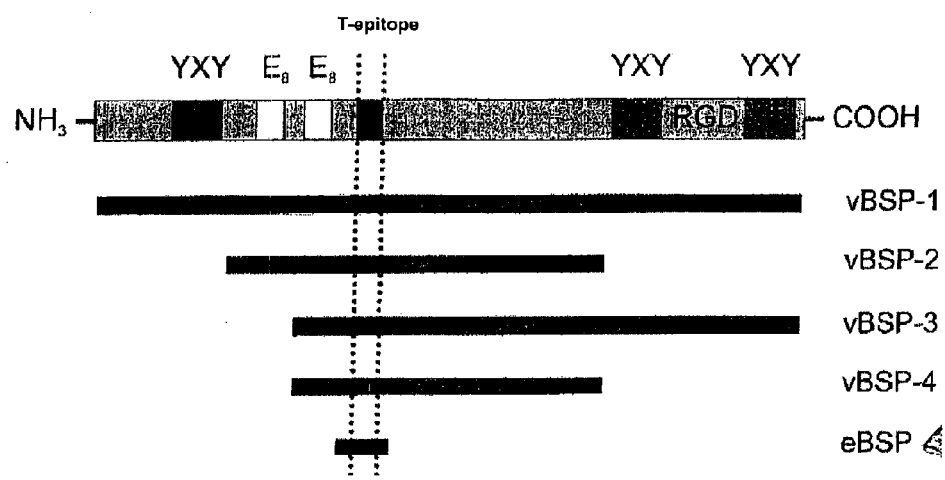
FIG. 2 shows a representation of generated BSP fragments for recombinant expression of BSP antigen segments on carrier bacteria; RGD: cell-binding motif; YXY: tyrosine-rich region; E8: glutamic acid-rich region; T-Epitop: BSP tumor epitope (BSP-position 125-130)
Figure 3A:
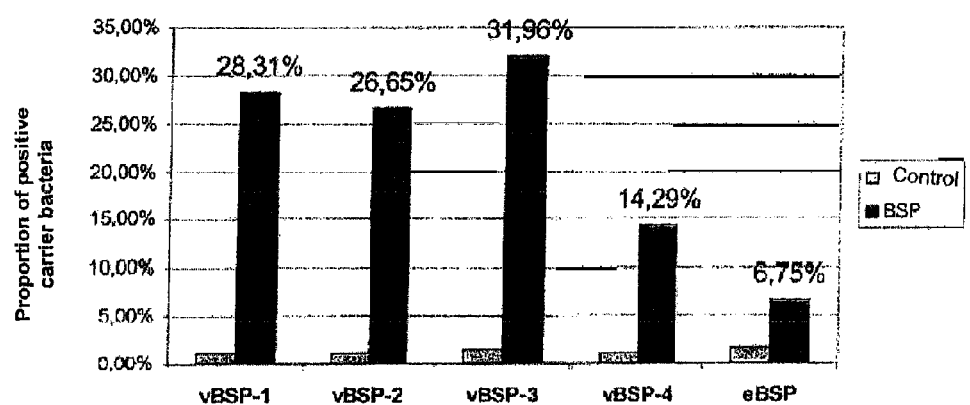
FIG. 3A shows a representation of the proportion of positive bacteria which after FACS analysis have on their surface functionally anchored BSP fragments (vBSP-1, -2, -3, -4 or eBSP), as evidenced by a tumor-epitope specific polyclonal antiserum (rabbit)—carrier bacteria with no BSP on the surface were used as negative control.
Figure 3B:
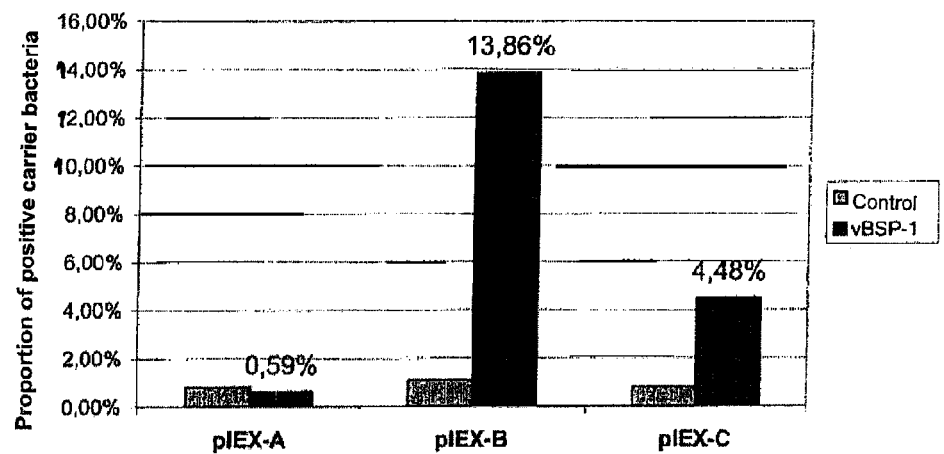
FIG. 3B-3G show representations of the proportion of positive bacteria, which after FACS analysis carry anchored vBSP-1, -2, -3, -4 and eBSP for various secretion signals (pIEX-A, -B, and -C), vectors (pIEX, pIUS), with a carrier protein (pXC-Add, PS-Add), as evidenced by monoclonal antibodies against the myc-tag—carrier bacteria with no recombinant protein on their surface were used as a negative control.
Figure 3C:
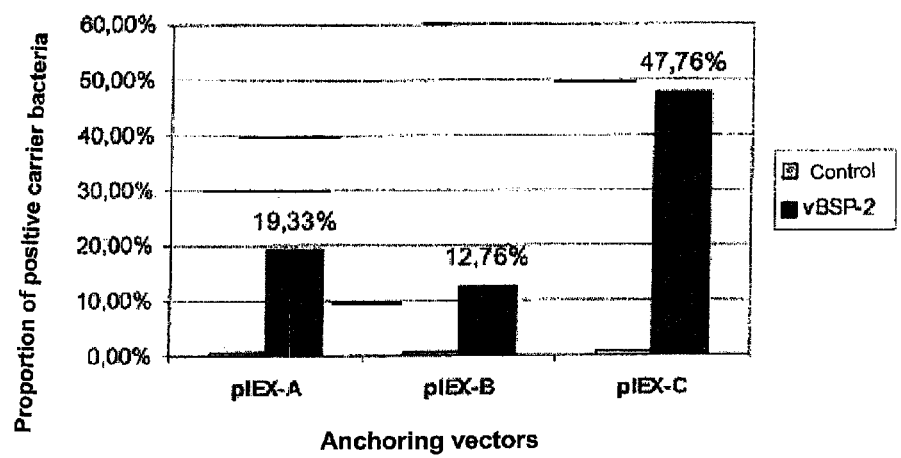
Figure 3D:
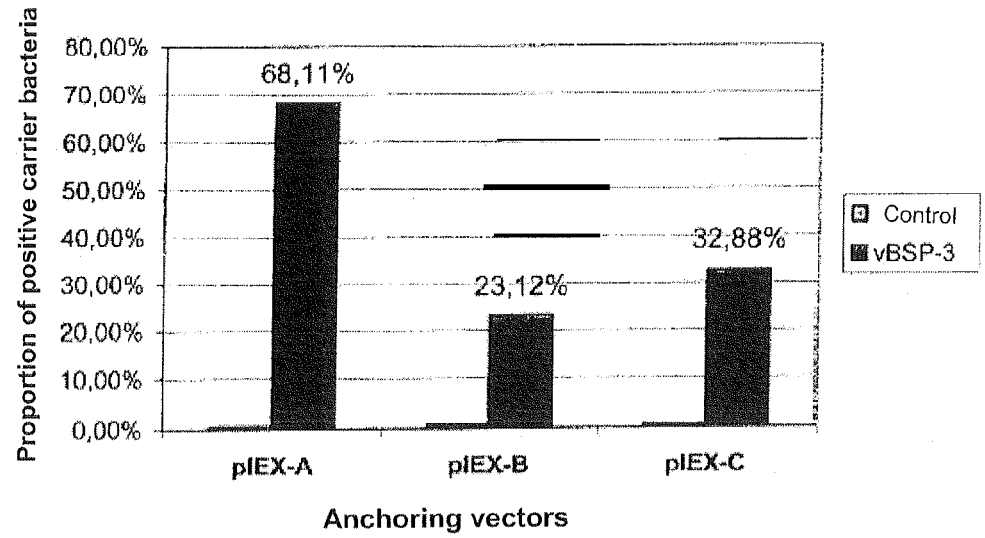
Figure 3E:
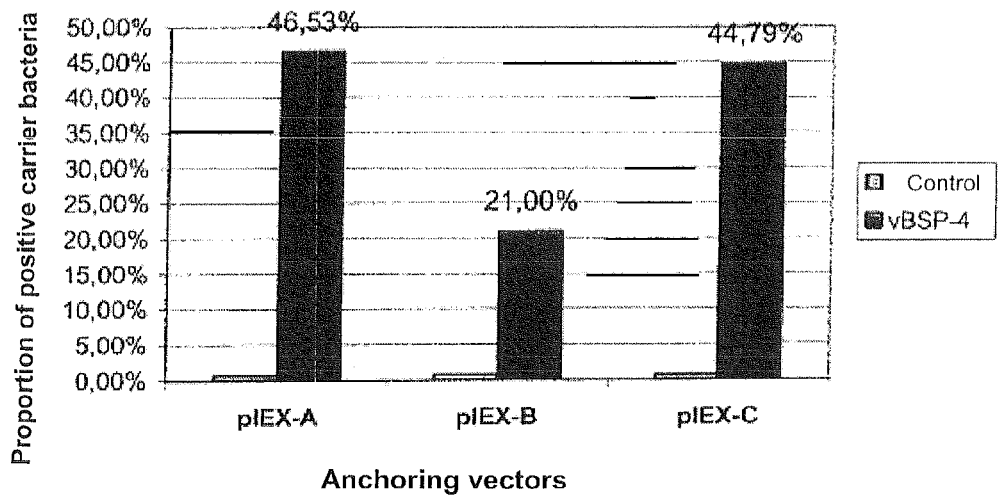
Figure 3F:
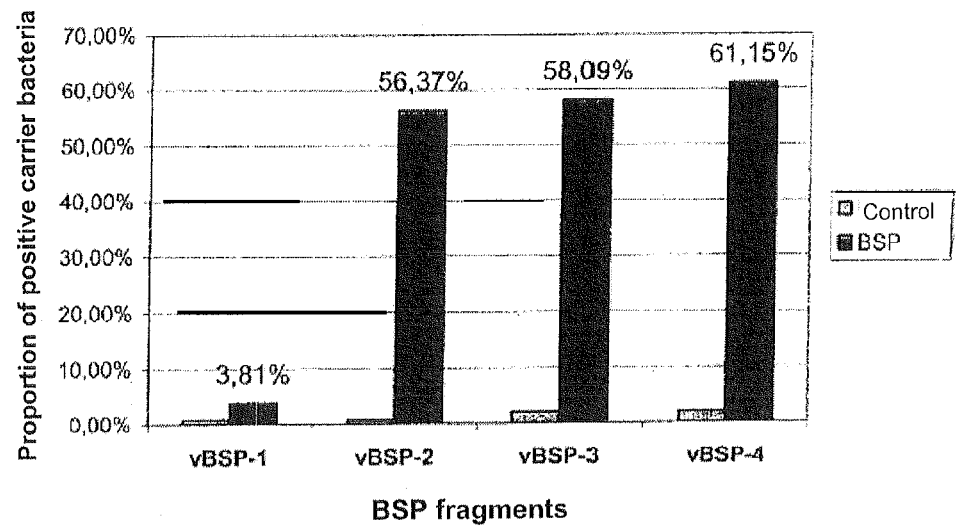
Figure 3G:
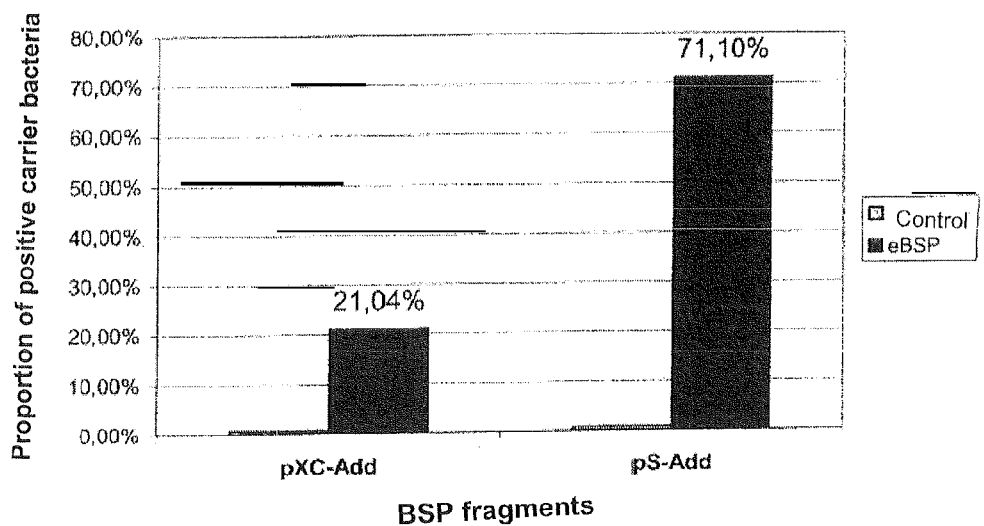

Osteotropic tumors of the prostate, breast, lung, kidney and thyroid differ from less malign tumors inter alia by the fact that they contain BSP expressing cells and can disseminate into the bone tissue. Even though the process of metastasis into bones is complex and not understood, the presence of tumorgenic BSP in serum allows for a safe prognosis of bone metastases. The presence of tumorgenic BSP in the bone matrix may further be used as a rating of the bone remodeling by bone metastases. BSP from tumor cells possesses other posttranslational modifications compared to endogenous BSP of normal osteoblasts. Thus, IgY-antibodies could be produced in chicken which specifically recognize a BSP secreted from cells of osteotropic tumors, called herein tumor-eBSP. In animal experiments, these antibodies are strikingly active against induced bone metastases of human cancer cells (WO 02/100899). The therapeutic composition of the invention for treatment and prevention of bone tumors elicits in the patient endogenous antibodies against BSP and in particular against tumor specific eBSP. Presumably, the so induced autoantibodies against tumorgenic eBSP interfere with the docking mechanism of the osteotropic cells from the primary tumor. Since BSP is bound and masked by factor H of the complement system, many eBSP expressing secondary cells of the primary tumor can evade from being attacked by the immune system and necrosis by the complement system. Also the bringing about of apoptosis would be very important. The death of autoreactive lymphocytes in the thyroid gland usually ensures that the immune system does not attack endogenous antigens. The therapeutic composition of the invention overcomes these false self-protection mechanisms, because, inter alia, an immune reaction against tumorgenic BSP from tumor cells is specifically induced, and the antibodies bind to an epitope of BSP, which remains free and accessible even when enshrouded by complement factor H from serum. The generated cell-mediated cytotoxicity causes a necrotic or apoptotic death of the target cells. Contrary to conventional therapeutic approaches, no tumor BSP specific antibodies are administered but a cell-mediated immunity produced in the patient by a combined xeno- and idio-immunization against a protein specific for tumors metastasizing into bones and presumably required for their dissemination into bones.

The therapeutic composition may contain dead or weakly pathogenic microorganisms, which contain a DNA sequence encoding BSP or a fragment thereof integrated in an episomal vector. Consequently, the therapeutic composition corresponds to a vaccine, or a live vaccine, in which a foreign BSP-encoding DNA is translated and expressed as BSP antigens and tumor-eBSP antigens, respectively, so that the patient develops antibodies against presented foreign BSP and tumor eBSP antigens. The so induced auto-immunity against tumor BSP presumably protects against the docking of metastasizing osteotropic cells of the primary tumor to the bone tissue and leads to a cell-mediated cytotoxicity against tumor BSP producing tumor cells. Both mechanisms evolve into a prophylactic and a therapeutic activity against bone metastases.

Further, the activity of the therapeutic composition may be enhanced and modulated by the addition of antibodies, especially anti-tumor BSP antibodies, ligands, especially RGD binding ligands, inhibitors which interact with adhesion molecules, membrane associated proteases or receptors mediating chemotaxis, for example chemokine receptors, as well as apoptosis inducing substances such as antibodies or proteins and peptides obtained from natural and artificial peptide libraries. Peptides from BSP and eBSP, which were made immunogenic by coupling with beta-alanine, appear to be especially promising.

Especially preferred is a therapeutic composition, in which the deactivated or weakly pathogenic micro-organisms lead to the expression of tumor eBSP in a form where the tumor eBSP is bound to a plasma membrane. The plasma membrane may be the plasma membrane of the micro-organism or the cell membranes of host cells of the patient, in which the genetic information of the tumor BSP had been specifically introduced.

Furthermore, it is useful to modify the introduced BSP-DNA in such a way that after expression, molecules similar to tumor BSP are obtained. The possible locations for a modification are especially on those positions on the DNA, which code amino acids, which are posttranslationally N or O-glycosylated. Hence posttranslational modifications may be removed through targeted point mutations. Namely, tumor BSP differs from endogenous BSP especially by a modified or incomplete posttranslational glycosylation. In order to increase the antigenicity of the cloned and expressed fragment, it may be advisable to couple several repeats thereof in line.

The amino acid sequence of human BSP contains four potential N-glycosylation sites at positions 88 (NTT), 161 (NGT), 166 (NST) and 174 (NGS). No consensus sequence is known with respect to O-glycosylation sites. All identified N-glycan structures can be found on BSP isolated from bones as well as on BSP from tumor cells. There are differences however in the percentage of the respective structures within the total amount of N-glycans. The major amount of N-glycans on BSP from bones consists of triantennary structures (58%) whereas for example they consist in the degenerate EBNA cell line of tetraantennary structures (48%). Furthermore, the human BSP molecule has at least eight O-glycosylation sites, five on the peptide 211-229 (TTTSP ... QVYR) and three at most on the peptide between amino acid 120 and amino acid 135 with the sequence TGLAA (SEQ ID NO: 3). Of these, the threonines in the sequence DATPGPT (SEQ ID NO: 9) are O-glycosylated on recombinantly expressed BSP from EBNA cells. A third O-glycosylation can be found on BSP isolated from bones. No third glycosylation location is present on recombinant BSP. This glycosylation site is presumably located on the TGLAA-BSP partial structure (SEQ ID NO: 3).

Because of the advantageous results obtained with antibodies against this partial structure of human BSP, the respective DNA sequence, coupled to a DNA encoding a carrier peptide and a membrane anchor (poly-His, Internalin-A sequences), was introduced as foreign DNA into the micro-organism and expressed—either in the micro-organism itself, or in the somatic transgenic host cells of the patient. The expressed tumor BSP fragments were recognized as foreign in mammals, because they were located on the membrane of a micro-organism, or on the surface of infected host cells. The so induced own antibodies bind to the BSP of the osteotropic tumor cells.

As said before, the preferred BSP peptide fragments are

```
                                                  SEQ ID NO: 1
X-YTGLAAIQLPKKAGD-Z

SEQ ID NO: 2
X-FSMKNLHRRVKIEDSEENGVFKYRPRYYLYKHAYFYPHLKRFPVQGSS

DSSEENGDDSSEEEEEEEETSNEGENNEESNEDEDSEAENTTLSATTLGY

GEDATPGTGYTGLAAIQLPKKAGDITNKATKEKESDEEEEEEEGNENEE

SEAEVDENEQGINGTSTNSTEAENGNGSSGVDNGEEGEEESVTGANAEGT

TETGGQGKGTSKTTTSPNGGFEPTTPPQVYRTTSPPFGKTTTVEYEGEYE

YTYDNGYEIYESENGEPRGDNYRAYEGEYSYFKGQGYDGYDGQNYYH

HQ-Z
``` wherein the highlighted threonine is not or incompletely glycosylated in BSP from tumor cell, or in a another way. SEQ ID NO: 2 may be modified as follows: position 179 Gly→Val; position 252 Val→Ala; position 254 Glu→Asp; Position 279 Asp→Gly.

In one embodiment of the invention the therapeutic composition induces the formation of endogenous antibodies against a BSP, which posttranslational glycosylation in the region of amino acids 120 to 135 (SWISSPROT: SIAL_HUMAN, Acc. No. P21815) is modified or incomplete compared to normal BSP from bones. Preferred is the induction of endogenous antibodies that recognize a hBSP epitope, which includes the amino acid sequence TGLAA (SEQ ID NO: 3) or YTGLAA (SEQ. ID NO: 4) and optionally sugar groups as well as a carrier molecule.

The vaccine of the present invention therefore results in endogenous antibodies against BSP from tumor cells. The so induced immunity therefore protects against the docking of metastasizing osteotropic tumor cells into bone tissue and assists in the development of a cell-mediated cytotoxicity against tumorgenic BSP producing cells.

The pharmaceutical composition in accordance with the present invention is especially useful in the treatment of tumors from the group comprising tumors of the prostate, breast, lung, kidney, thyroid, circulatory system, lymphoid system, cardiovascular system, neurological system, respiratory tract, digestive tract, endocrine system, skin including adnexa, musculoskeletal system and urogenital system.

A further aspect of the invention relates to a process for the development of vaccines, especially against tumors in general and osteotropic tumors, which metastasize into bones. This process comprises the following steps: (i) identification of a protein relevant for the condition such as e.g. BSP; (ii) formation of carrier organisms with one or more chosen regions (immune tags) of the protein relevant for the condition, which express and carry on the cell surface, anchored to the cell membrane, the immune tag; (iii) testing of preferably inactive carrier organisms, for whether they induce an immune reaction against the immune tags of the protein relevant for the condition; (iv) examination of a number of subjects, including sick and healthy patients, for antibodies against said immune tags of the protein relevant for the condition, for example by a screening of blood sera and (v) selecting carrier organisms with immune tags on the surface as vaccine bacteria in accordance with the finding as to which subjects and with which anamnesis, including recovered healthy patients, possess antibodies that bind to one or more immune tags of said protein relevant for the condition. As steps (i) to (iii) are relatively fast and most importantly can be carried out in parallel, and as blood sera for use in step (iv) and corresponding health records (v) are available by the million, useful vaccine bacteria with anchored immune tags can be produced and identified by a statistical analysis of the health records. The occurrence of natural antibodies against one or more immune tags of said protein relevant for the condition in any blood serum is already an indication per se that the one or more selected immune tags are medically relevant. The relevance may be determined by comparing the corresponding anamneses. As step (iv) can done by analytical machines for numerous and abundantly available blood sera, relevant and non-relevant antigen fragments can readily be identified by statistical analysis without the need for a medical anamnesis. In particular blood sera of patients with spontaneous recovery or a very mild course of disease should be tested in the search for tumor relevant immune tags.

EXAMPLES

Example 1

Expression Vectors and Micro-Organisms for Immunization

The cDNA of human BSP (SEQ. ID NO: 2), respectively the below mentioned BSP fragments were cloned in the polycloning site of an episomal pSOG shuttle vector (Machner et al., J. Biol. Chem., 2001, 276 (43), 40096; L. W. Fisher et al., J. Biol. Chem., 1990, 265(4), 2347-51). In order to achieve an anchoring of the cloned heterologous BSP antigens on the surface of the *Listeria*, an expression and anchoring cassette was built into the *E. coli/Listeria* shuttle vector (erythromycin resistance, ColE1 origin of replication, gram-positive minimal replicon for gram-positive bacteria). All components of the expression and anchoring cassette were amplified using PCR from the respective organisms and cloned into the shuttle vector. The relative order of the individual components of the expression and anchoring cassette is shown in FIG. 8.

The promotor (pind) of the *Listeriolysin* gene from *Listeria monocytogenes* was used for the expression of recombinant peptides (Mengaud et al. Infect. Immun. 1989, 57:3695). The promotor was cloned together with the 5'-untranslated region of the *Lysteriolysin* gene (Accession No. NC003210) upstream of a nucleotide sequence encoding the signal peptide (SS) of *Listeriolysin* (LLO—protein sequence in Swiss-Prot: Q724L1; nucleotide sequence—Genbank Accession Nos. P13128, X15127). The identification of the signal sequences was done in accordance with the literature and using the software SignalP vs. 2.0 (Nielsen et al., Protein Engineering, 1999, 12:3). The signal peptide, which is usually about 25 amino acids long, transports the recombinant peptides across the cell membrane of the carrier bacterium and is then split off. In one embodiment were upstream and downstream of the genes encoding the BSP epitopes further nucleotide sequences introduced which encoded two immune tags (S-tag of Novagen, Darmstadt; upstream, myc-tag of NanuTec GmbH, Frankfurt; downstream). When expressed the S-tag and myc-tag facilitate the immunological characterization of the anchoring of the BSP epitopes on the surface of the *Listeria*. In order to achieve a secure anchoring of the recombinant heterologous antigen determinant on *Listeria*, a sequence from Internalin A (InlA) of *L. monocytogenes* was integrated downstream of the myc-tag. The introduced anchor included the positions 677-800 of the InlA (Swiss-Prot: Q723K6).

Between the two immune tags were then cloned two nucleotide sequences which encoded the BSP tumor epitopes as monomer or as polymer comprising two to six copies of the BSP tumor epitope. The BSP tumor epitope has the amino acid sequence -EDATPGTGYTGLAAIQLPKKAG- (eBSP) (SEQ ID NO: 10). The different tumor epitopes were linked via a short spacer with the amino acid sequence -SGGGGSA- (Sp) (SEQ ID NO: 8). The tumor epitope and the spacer were amplified by a PCR and cloned into the anchoring plasmid pIUSind using standard methods.

Hence, the constructs in the example of pIUSind-mBSP1x-6x in *Listeria* led to the expression of fusion peptides, which consisted of an N-terminal signal peptide, an S-tag, a (pIUSind-mBSP1x) or several BSP epitopes (pIUSind-mBSP2x-6x), an myc-tag and an anchoring structure. The signal peptide effected that the fusion peptide got translocated out of the carrier bacterium while the anchoring structure of the Internalin-A provided for a "covalent" anchoring of the BSP epitope to the cell wall of the bacterium. The correct reading frame was verified by DNA sequencing and expression; the fusion peptide was recognized by anti-hBSP-antibodies and also by therapeutic IgY antibodies. The *Listeria* pIUSind-mBSP5x (DSM 18306) and *Listeria* pIEx-A-vBSP3 (DSM 18305), which contain the vectors, were deposited with the DSMZ (German National Resource Centre for Biological Material, Braunschweig).

Example 2

Therapeutically Active BSP Antigen Structures

The epitopes of therapeutically active anti-BSP-IgG and -IgY were mapped to characterize more closely the antigens, respectively haptens, to which they bind in the immunization experiments against tumorgenic BSP.

TABLE 1

BSP epitopes of therapeutically active anti-BSP-IgG and -IgY globulins

| Position of the structural fragment in BSP (Position, including Leader) | Amino acid sequence | Reaction strength chicken - rabbit IgY | IgG |
|---|---|---|---|
| 112-123 - SEQ ID NO: 11 | LeuGlyTyrGlyGluAsp-AlaThrProGlyThrGly | – | ? |

TABLE 1-continued BSP epitopes of therapeutically active
anti-BSP-IgG and -IgY globulins

| Position of the structural fragment in BSP (Position, including Leader) | Amino acid sequence | Reaction strength chicken - rabbit | |
|---|---|---|---|
| | | IgY | IgG |
| 216-227 - SEQ ID NO: 12 | GluThrGlyGlyGlnGly-LysGlyThrSerLysThr | - | ? |
| 300-311 - SEQ ID NO: 13 | PheLysGlyGlnGlyTyr-AspGlyTyrAspGlyGln | - | ? |
| 130-144 - SEQ ID NO: 14 | IleGlnLeuProLysLys-AlaGlyAspIleThrAsn-LysAlaThr | +/- | + |
| 124-138 - SEQ ID NO: 01 | TyrThrGlyLeuAlaAla-IleGlnLeuProLysLys-AlaGlyAsp | - | ++ |
| 137-151 - SEQ ID NO: 15 | GlyAspIleThrAsnLys-AlaThrLysGluLysGlu-LysGluSerAspGlu | - | + |
| 280-317 - SEQ ID NO: 16 | SerGluAsnGlyGluPro-ArgGlyAspAsnTyrArg-AlaTyrGluAspGluTyr-SerTyrPheLysGlyGln-GlyTyrAspGlyTyrAsp-GlyGlnAsnTyrTyrHis-HisGln | ++ | + |
| Human bone BSP | | +++ | +++ |

The results show that the known chicken antibodies preferably bind to the terminal sequence of the BSP whereas the rabbit antibodies bind over a larger range. Therapeutically relevant regions of the human BSP are therefore:

TyrThrGlyLeuAlaAlaIleGlnLeuPro    SEQ ID NO: 1
LysLysAlaGlyAsp                   (positions 124-138)

ThrGlyLeuAlaAla                   SEQ ID NO: 3
                                  (positions 125-130)

TyrThrGlyLeuAlaAla                SEQ ID NO: 4
                                  (positions 124-130)

TyrGluSerGluAsnGlyGluProArgGly    SEQ ID NO: 6
AspAsnTyrArgAlaTyrGluAsp          (positions 278-295)

LeuLysArgPheProValGlnGlyGly       SEQ ID NO: 7
                                  (N-Terminus)

For a secondary delimitation of the tumor relevant BSP structures, the following larger fragments of human BSP were cloned and expressed in bacteria:

vBSP-1: 301 amino acids of the hBSP sequence between positions 17 and 318, which represent the full sequence of human BSP (without the signal sequence).

vBSP-2: 200 amino acids between positions 57 and 257—vBSP-2 contains no tyrosine-rich regions and no RGD sequence. vBSP-2 starts immediately after the first tyrosine-rich region and finishes immediately before the second tyrosine-rich region.

vBSP-3: 234 amino acids between positions 84 and 318. vBSP-3 does not contain the first glutamic acid rich region and extends until the C-terminal of the BSP.

vBSP-4: 174 amino acids between positions 84 and 257. vBSP-4 has been shortened by the first glutamic acid rich region and all tyrosine-rich regions.

eBSP: 22 amino acids (-EDATPGTGYTGLAAIQLPKKAG-(eBSP)—SEQ ID NO: 10) between positions 115 and 137, including one antigenic determinant of BSP which has been identified as tumor epitope.

FIG. 2 shows the position of the above-mentioned fragments in the BSP protein in relation to the other relevant structures.

Example 3*

Generation of the BSP Constructs Needed for the Anchoring

The DNA sequences of the BSP fragments vBSP-1, -2, -3, -4 and eBSP (Example 2, FIG. 2) were amplified using PCR and cloned into the above described shuttle vectors. The cloning of the genes was verified by sequencing and then the genes sub-cloned into various secretion and anchoring vectors. The BSP fragments vBSP-1, -2, -3 and -4 were fused at the C-terminus with an immune tag (myc-tag) to facilitate the detection of anchored fragments. The only 22 amino acid long fragment containing eBSP was fused to the N-terminus of a bacterial carrier protein to avoid that the eBSP because of its small size does not protrude from the bacterial cell wall or is masked by other molecules in the cell wall. The clones detailed in table 2 were generated:

TABLE 2

| anchoring construct | anchoring vector | BSP fragment | carrier protein |
|---|---|---|---|
| pIEX-A-vBSP1 | pIEX-A | vBSP-1 | no |
| pIEX-A-vBSP2 | pIEX-A | vBSP-2 | no |
| pIEX-A-vBSP3 | pIEX-A | vBSP-3 | no |
| pIEX-A-vBSP4 | pIEX-A | vBSP-4 | no |
| pIEX-B-vBSP1 | pIEX-B | vBSP-1 | no |
| pIEX-B-vBSP2 | pIEX-B | vBSP-2 | no |
| pIEX-B-vBSP3 | pIEX-B | vBSP-3 | no |
| pIEX-C-vBSP1 | pIEX-C | vBSP-1 | no |
| pIEX-C-vBSP2 | pIEX-C | vBSP-2 | no |
| pIEX-C-vBSP3 | pIEX-C | vBSP-3 | no |
| pIUS-vBSP1 | pIUS | vBSP-1 | no |
| pIUS-vBSP2 | pIUS | vBSP-2 | no |
| pIUS-vBSP3 | pIUS | vBSP-3 | no |
| pXC-Add-eBSP | pXC-Add | EBSP | yes |
| pS-Add-eBSP | pS-Add | EBSP | yes |

All clones were generated in *E. coli* and subsequently transformed in carrier bacteria.

It was then further examined whether each of the BSP fragments can be expressed, secreted and functionally anchored onto the bacterial host. The "functional anchoring" of the BSP fragments with respect to the planned application of the vaccine bacteria required that the BSP fragments were expressed in and translocated out of the carrier bacteria, and finally covalently anchored on the surface of the bacteria. The anchored BSP fragments contained inter alia the BSP tumor epitope, which was recognized by the tumor epitope specific antiserum. By this step it was assured that the BSP tumor epitope was actually presented on the surface of the carrier bacteria and that it could induce a tumor epitope specific immune response when vaccine bacteria were administered for active immunization.

In order to achieve a functional anchoring of the BSP fragments, the generated BSP anchoring constructs were transformed into carrier bacteria and the respective BSP fragments anchored on the bacteria. The detection of a functional anchoring was carried out in the flow through cytometer with a polyclonal antiserum "Anti-Human Bone Sialoprotein (amino acids 108-122) Antibody", which is commercially available from Immundiagnostik AG, Bensheim (Cat.-No. A4219.2, Lot H3150503). This polyclonal antiserum detected the tumor epitope of BSP. A positive result with this antiserum therefore showed the "functional anchoring" of each of the BSP fragments as heterologous *Listeria* surface antigens for active immunization.

Figure 4:
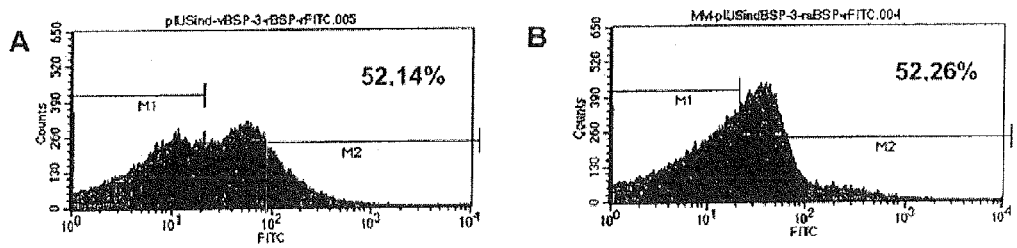
FIG. 4 shows diagrams of a flow-through cytometry of carrier bacteria for functionally anchored BSP fragment on the surface prior inactivation—A) anchoring of vBSP-3 on carrier bacteria grown in BHI culture medium; B) anchoring of vBSP-3 on carrier bacteria grown in minimal medium, and the fluorescence activated cell sorting (FACS) being carried out with polyclonal rabbit anti-tumor eBSP antibodies and carrier bacteria without BSP determinants on the surface as control.
Figure 5:
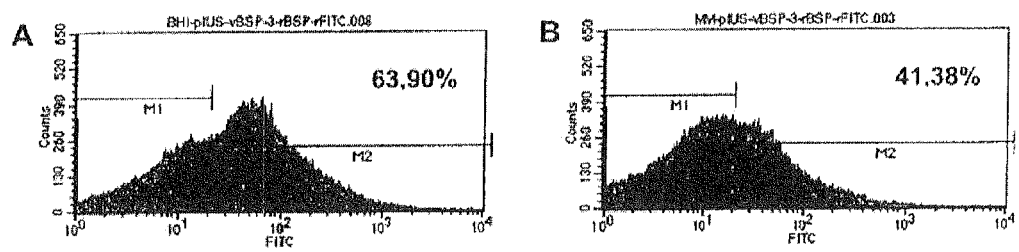
FIG. 5 shows diagrams of the flow-through cytometry of carrier bacteria in accordance with FIG. 4 post inactivation—A) anchoring of vBSP-3 when grown in BHI-medium; B) anchoring of vBSP-3 when grown in minimal medium.

Preliminary works showed that the following BSP fragments were functionally expressed in bacteria and also in *Listeria*. Additionally, they were secreted out of the carrier bacteria and functionally anchored on them. Hence, selected fragments of hBSP were coupled onto *L. monocytogenes* and the bacteria were tested for whether they induced an immune reaction against the cloned BSP fragment, the tumorgenic BSP epitope and finally against tumor cells. For this, at first, signal sequences were identified, which efficiently secreted the identified BSP fragments out of the bacteria, but only in such a way that the BSP remained anchored on the *Listeria*. The anchoring efficiency of the selected BSP fragments should be above 40%—if tested with antibodies against these immune tags. Further, conditions were identified, under which the selected BSP fragments would remain anchored stably and reproducibly on the bacteria. Finally, the conditions for propagation and deactivation of the BSP bacteria for immunizations were determined. In total, the anchoring efficiency was ≧40%. However, the professional will have to determine the optimum breeding conditions and the best suited anchoring sequences for each bacterial strain in the usual way. More specifically, the following fragments of human BSP were anchored on the surface of carrier bacteria. The anchoring efficiencies are shown in Table 3.

TABLE 3

| Anchoring efficiencies | | |
|---|---|---|
| BSP Fragment | Vector | Anchoring efficiency |
| vBSP-1 | pIEX-B | >13% |
| vBSP-2 | pIUS | >56% |
| vBSP-2 | pIEX-C | >47% |
| vBSP-3 | pIUS | >58% |
| vBSP-3 | pIEX-A | >68% |
| vBSP-4 | pIUS | >61% |
| vBSP-4 | pIEX-A | >46% |
| eBSP | pS-Add | >71% |

FIGS. 3A-G show the results obtained with these experiments schematically and in direct comparison with respect to fragment, anchoring vector, and breeding conditions. In order to anchor BSP fragments on the surface of carrier bacteria, two different vector systems were used. While the pIEX vector systems were designed for the anchoring of heterologous proteins on carrier bacteria during breeding in a fully synthetic culture medium, the pIUS vectors were suited for the anchoring of proteins during the breeding of the carrier bacteria in complex media.

BSP fragment vBSP-1 was anchored onto carrier bacteria most efficiently by the secretion signal of vector system pIEX-B. The anchoring efficiency of vBSP-1 was comparatively low with 13.86% (see FIG. 3B). This is probably due to the fact that vBSP-1 is produced in the carrier bacteria only with comparatively low expression rates. Studies in other laboratories have shown that in most cases full length BSP (~vBSP-1) is not produced at all in prokaryotic expression systems. Because full length BSP (vBSP-1) had been anchored on the carrier bacteria in the system used, it can be assumed that its anchoring on the surface of bacteria has a stabilizing effect on the full length BSP. Subsequently, BSP fragments vBSP-1, -2, -3 and -4 were functionally expressed in carrier bacteria, secreted out of the carrier bacteria and also functionally anchored on the surface of carrier bacteria. Finally, the tumor epitope eBSP was expressed as fusion protein in carrier bacteria, secreted and functionally anchored. The functional anchoring was proven inter alia by FACS and monoclonal antibodies, which recognize the immunological tag (myc-tag) fused to the C-terminal end of the BSP fragments.

Dependent on the specific biochemical properties of the protein to be anchored, different signal sequences are required for obtaining optimal secretion and anchoring of heterologous proteins on the carrier bacteria. The inventors therefore analyzed in a test series different signal sequences for their ability to secret and anchor the BSP fragments.

In subsequent tests hBSP fragments vBSP-3 and eBSP were primarily studied. The structure and position of these fragments in human BSP are shown in FIG. 2. These two BSP determinants are particularly advantageous since vBSP-3 contains along with the tumor epitope and two C-terminal tyrosine-rich regions further the RGD motif. A role in the induction of apoptosis has been attributed to the RGD motif and immune reactivities against the RGD motif, respectively. Apart from the actual tumor epitope no further BSP structures were anchored as an antigen when eBSP or multimers of eBSP were used. This reduces the risk that the immunization leads to reactivities against healthy cells which express native BSP.

Example 3*

Anchoring of hBSP Fragments

Anchoring of vBSP-3

We determined the conditions for a stable and reproducible anchoring of the vBSP-3 fragment. For this we tested the following constructs for their ability to provide a functional anchoring of the vBSP-3 fragment on the carrier bacteria. The functional anchoring was tested by flow-through cytometry using polyclonal antibodies against amino acids 108-122 of human bone sialoprotein (Immundiagnostik AG, Bensheim, Del.: Cat-No. A4219.2, Lot H3150503). These polyclonal antibodies recognize an epitope on BSP, which is only present on BSP from tumor cells (heretoforth referred to as tumor epitope). A positive result with these antibodies represents a functional BSP fragment as an antigen for an active immunization against tumorgenic BSP.

TABLE 4

| Anchoring constructs | | |
|---|---|---|
| Anchoring construct | Anchoring vector | BSP fragment |
| pIEX-A-vBSP3 | pIEX-A | vBSP-3 |
| pIEX-B-vBSP3 | pIEX-B | vBSP-3 |
| pIEX-C-vBSP3 | pIEX-C | vBSP-3 |
| pIUS-vBSP3 | pIUS | vBSP-3 |

The best results were got with the anchoring constructs pIEX-A-vBSP-3 and pIUS-vBSP-3 (see FIGS. 3D and 3F). Optimal functional anchoring of vBSP-3 was achieved by varying the breeding and anchoring conditions both by cultivation in BHI medium (Brain-Heart-Medium) as well as in a synthetic minimal medium (FIGS. 4 and 5). The achieved anchoring efficiency of greater than 52% for cultivation in BHI and minimal media must be considered excellent (FIGS. 4A and B). Hence, vBSP-3 bacteria could be grown in BHI medium as well as in minimal media. The BHI-medium gave the advantages of fast growth and high bacterial density in the medium so that a high number of vaccine doses can be produced within a short period. On the other hand, vBSP-3 bacteria grew slower and less dense in minimal medium. However, there is no danger of contamination of the vaccines with BSE or TSE when the cultivation is done in a synthetic minimal medium. This can be a decisive advantage in the future use of vBSP-3 bacteria in humans.

Example 4

Deactivation of the Recombinant *Listeria* while Preserving the Anchoring of hBSP Fragments Bacteria which carry recombinant proteins anchored to their surfaces are genetically modified organisms (GMO). The immunization using GMOs, even in animal models, require very extensive safety precautions. On the other hand, deactivated vaccine bacteria are not GMOs any more and may therefore be treated like conventional vaccines.

Therefore, conditions were identified, with which the carrier bacteria may be safely deactivated, but where at the same time vBSP-3 remains safely anchored on the bacterial surfaces. FIG. 5 shows the anchoring efficiency of vBSP-3 on deactivated vaccine bacteria when grown in BHI medium (FIG. 5A) and minimal medium (FIG. 5B). As can be derived from FIG. 5, the carrier bacteria could be safely deactivated by the addition of formaldehyde while the vBSP-3 remained functionally anchored on the surfaces of the killed bacteria and was recognized by rabbit antibodies specific for tumor epitope. The anchoring efficiency of the vBSP-3 on deactivated carrier bacteria was approximately 64% when grown in BHI medium and about 41% when grown in minimal medium (see FIG. 5), which is outstanding for such types of epitopes.

Example 5

Anchoring of the BSP Fragments vBSP-2 and vBSP-4

The vBSP-3 fragment contains in addition to a glutamic acid rich region the two tyrosine-rich regions at the C-terminus and the RGD motif of BSP. In comparison thereto the BSP fragments vBSP-2 and vBSP-4 lacked the tyrosine-rich regions and the RGD motif (see FIG. 2). For optionally characterizing the relevance of respective functional regions of the BSP on the immune response of the vaccinated individual, vBSP2 and vBSP4 vaccine bacteria were generated.

Figure 6:
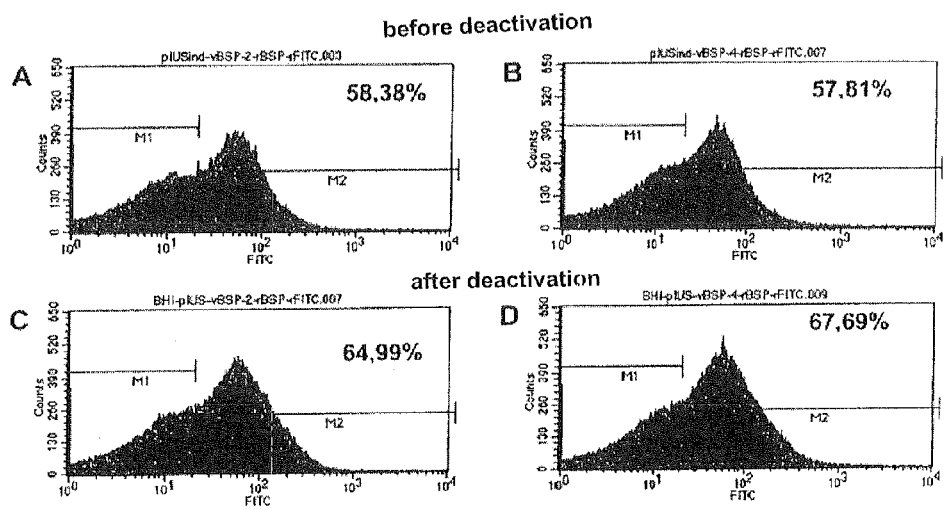
FIG. 6 shows diagrams of the flow-through cytometry of carrier bacteria prior and post inactivation for functionally anchored BSP fragment vBSP2 or vBSP 4—anchoring of vBSP2 when carrier bacteria were grown in BHI culture medium A) prior inactivation and C) post inactivation; anchoring of vBSP4 when carrier bacteria were grown in BHI medium B) prior inactivation and D) post inactivation.

FIG. 6 shows the anchoring efficiency of BSP fragments vBSP-2 (A and C) and vBSP-4 (B and D) on carrier bacteria prior and post deactivation using optimal experimental conditions. FIG. 6 shows that deactivated vaccine bacteria could be produced which possessed anchoring efficiencies of close to 65% (vBSP-2 vaccination bacteria) and 68% (vBSP-4 vaccination bacteria), respectively. Thus the produced vBSP-2 and vBSP-4 vaccine bacteria could well be used in immunization experiments.

Example 6

Anchoring of the BSP Tumor Epitope on *Listeria*

Figure 7:
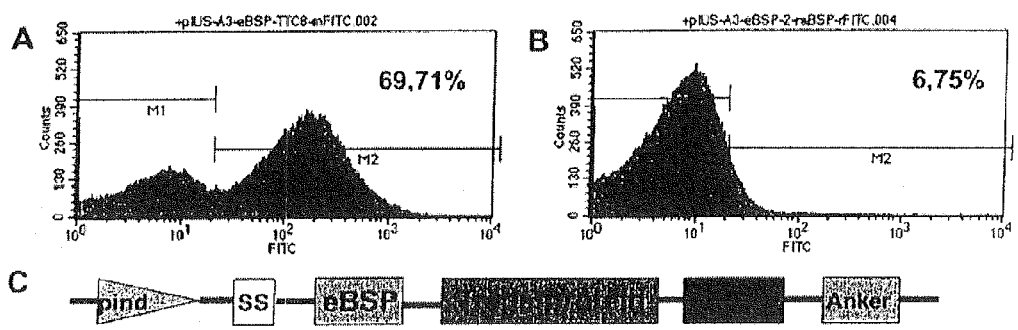
FIG. 7 shows a flow-through cytometry of carrier bacteria for functionally anchored tumor eBSP epitope, fused with a carrier protein, when detected A) with a monoclonal antibody against the carrier protein, B) with polyclonal tumor-epitope specific rabbit antibodies, and carrier bacteria without any recombinant protein on their surface as control—C) schematic representation of the expression cassette of the eBSP construct, SS: signal sequence, S-Tag: immune tag, myc-Tag: immune tag; Anker: anchor sequence.

The initially produced anchoring constructs for the eBSP tumor epitope possessed only anchoring efficiencies of about 6% to 7%, as determined with antibodies against eBSP (FIG. 7B). The low anchoring efficiency however was not the result of a bad anchoring efficiency of the fusion protein with eBSP on the bacteria. The fusion protein possessed an anchoring efficiency of nearly 70%, as determined using an antibody against the carrier protein. As the BSP tumor epitope had been anchored by way of a fusion protein with a carrier protein on the bacteria, the BSP tumor epitope must be present on the bacteria in the same proportion as the carrier protein and the anchoring efficiencies of the carrier protein and the BSP tumor epitope must be identical. Notwithstanding, the measured anchoring efficiency of the carrier protein was close to 70%, and the anchoring efficiency of the BSP tumor epitope was just below 7% (FIG. 7A). It is probable that the affinity of the tumor epitope BSP specific antibody was significantly lower than the affinity of the monoclonal antibody for the carrier molecule, or that the tumor epitope was shielded by the cell membrane due to its reduced size and therefore not recognized by the antibody. It is also possible that the tumor epitope was shielded by the carrier protein. There is always a chance that a singular small epitope (such as the BSP tumor epitope) is not fully accessible. In that case the immunogenicity of such vaccination bacteria against the tumor epitope would be low. In order to improve the probability of a successful vaccination using eBSP vaccination bacteria, the tumor epitope was anchored onto the carrier bacteria as multimers.

Example 7

Generation of Constructs for the Anchoring of Multimeric BSP Tumor Epitopes

Figure 8:
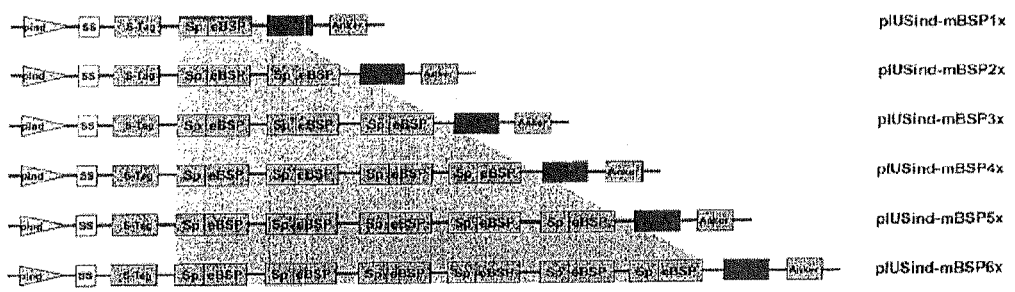
FIG. 8 shows a representation of the expression cassette of the anchoring constructs pIUSInd-mBSPIx-6x: pInd: Promotor; SS: signal sequence; S-Tag: immunological tag; SP: Spacer (SGGGGSA)—SEQ ID NO: 8; myc-Tag: immune tag; Anker: anchor sequence.
Figure 9:
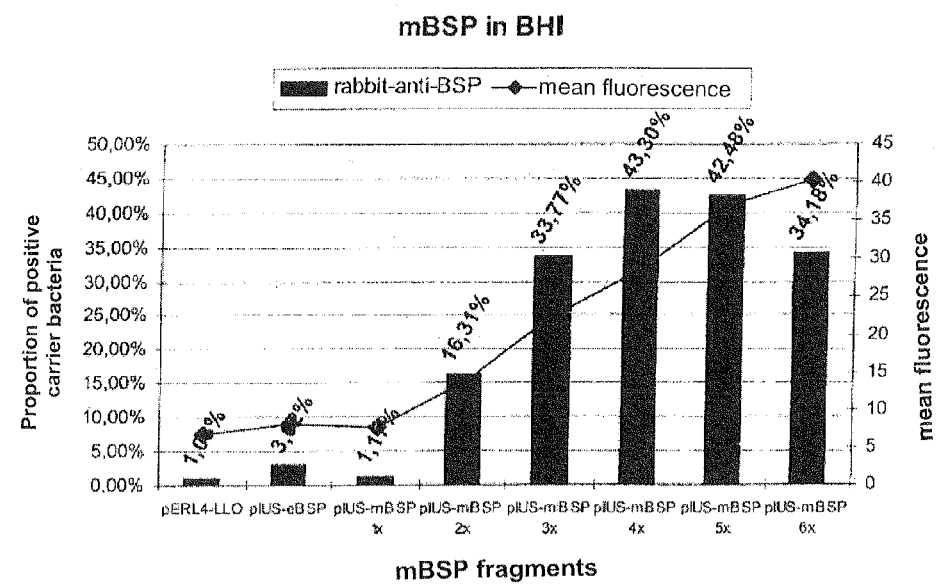
FIG. 9 shows a flow-through cytometry of carrier bacteria with various copy numbers of BSP tumor epitopes when grown in BHI-medium—functionally anchored BSP tumor epitope on the surface was detected with tumor-epitope specific rabbit antibodies, and carrier bacteria without BSP immune tags on the surface (pERL4-LLO) were used as control: pIUS-eBSP anchors only one and pIUS-mBSP-1x-6x anchors multimers (1-6) of the BSP tumor epitope on the surface of the carrier bacteria.
Figure 10:
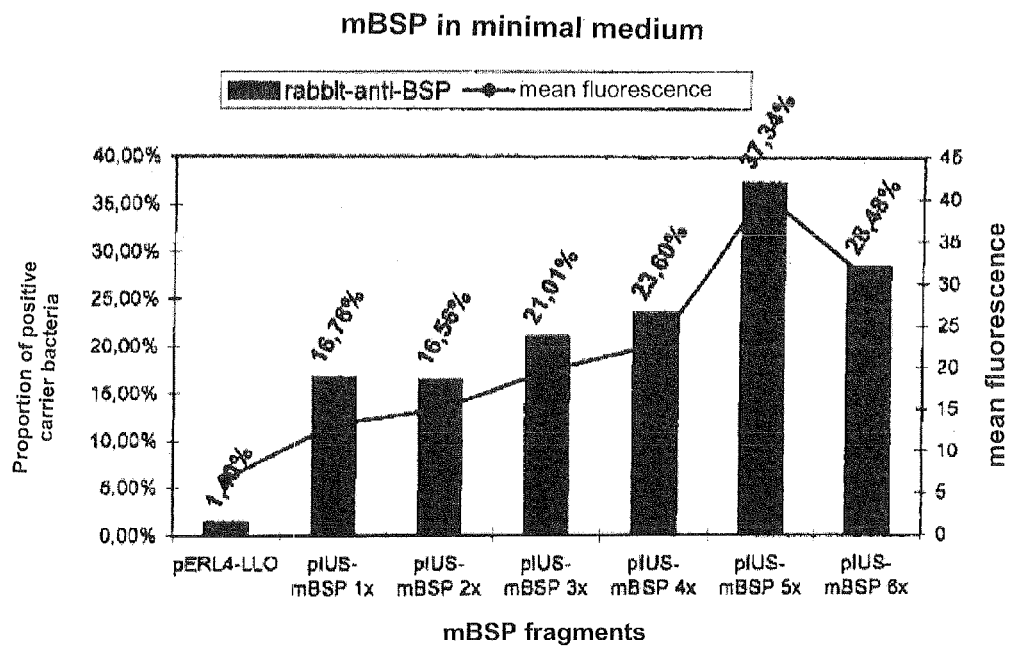
FIG. 10 shows the diagram of a flow-through cytometry of carrier bacteria grown in minimal medium for surface-anchored functional BSP tumor epitopes in various numbers, detected with a tumor eBSP antiserum from rabbit, and carrier bacteria without BSP immune tags on the surface (pERL4-LLO) as control—pIUS-mBSP-1x-6x: anchoring of a BSP tumor epitope as a multimer (1x-6x) on carrier bacteria.

We generated anchoring constructs that anchor the eBSP tumor epitope one to six-fold on the surfaces of carrier bacteria (FIG. 8). A 7 amino acid spacer (-SGGGGSA-) (SEQ ID NO:8) was cloned between every tumor epitope to ensure free flexibility of movement for each BSP tumor epitope. A comparative analysis of the anchoring of multimeric BSP epitopes for cultures in BHI medium (FIG. 9) and minimal medium (FIG. 10), respectively, showed that the measurable anchoring efficiency of multimeric BSP epitopes increases between the monomer to the pentamer from below 10% to above 40%, but that it was slightly reduced in the case of the anchoring of the eBSP hexamer. On the other hand, the mean fluorescence of the vaccine bacteria increased further in the case of the anchoring of 6x-eBSP tumor epitope, at least when grown in BHI-medium. This suggests that in the case of the eBSP tumor epitope hexamer fewer cultured bacteria carried tumor epitopes anchored to their surface, but that a higher number of tumor epitopes were anchored on each bacterium compared with vaccine bacteria carrying 4x and 5x multimeric eBSP tumor epitopes. Animal experiments will show which of the vaccine bacteria carrying 4x-, 5x- or 6x-multimeric eBSP have the highest immunogenicity.

Figure 11:
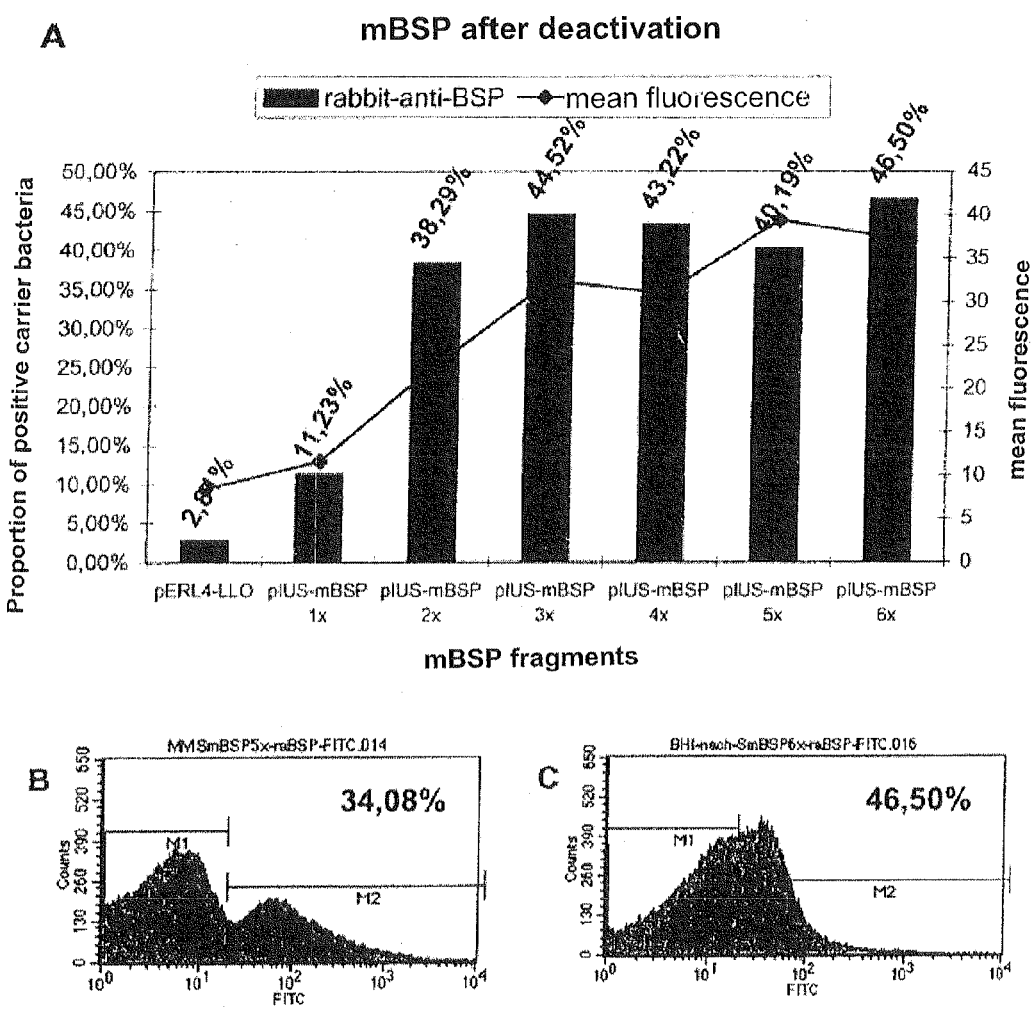
FIG. 11 shows the diagram of a flow-through cytometry of carrier bacteria post inactivation for surface-anchored functional BSP tumor epitopes in various numbers, when detected with a rabbit tumor eBSP antiserum, and carrier bacteria without BSP immune tags on the surface (pERL4-LLO)—A) pIUS-mBSP-1x-6x: anchored constructs, which have the BSP tumor epitope anchored as a multimer (1x-6x) on carrier bacteria as shown in FIG. 8; B) FACS-diagram of inactivated carrier bacteria grown in minimal medium, which carry the BSP tumor epitope as a 5-multimer anchored to the surface; C) FACS diagram of inactivated carrier bacteria grown in BHI-medium, which carry the BSP tumor epitope as a 6-multimer anchored to the surface.

Repetitive DNA regions of 100% sequence homology are often unstable. Even though the generated constructs pIUS-mBSP1x-6x contained repetitive DNA regions, no instability was observed for the anchoring constructs during the experiments. Thus, stable vaccine bacteria could be produced which had a measured anchoring efficiency of more than 40% (see FIG. 9). The vaccine bacteria which carried the BSP tumor epitope as a 3-fold, 4-fold, 5-fold or 6-fold multimer anchored to their surface displayed even after deactivation a measurably high anchoring efficiency of above 40% (FIG. 11). The anchoring rates were generally slightly higher for cultures grown in BHI medium than for cultures grown in minimal medium. Notwithstanding, vaccine bacteria with multimeric BSP tumor epitopes could be obtained both in BHI medium (FIG. 11, C) as well as in minimal medium (FIG. 11, B). Thus vaccine bacteria could be provided which carried anchored to their surfaces BSP fragments or multimers of the tumor epitope. Table 5 below shows that anchoring rates of sometimes well above 40% were achieved for all vaccine bacteria.

TABLE 5

Anchoring fragments and efficiencies

| BSP FRAGMENT | ANCHORING EFFICIENCY | |
|---|---|---|
| | BEFORE DEACTIVATION | AFTER DEACTIVATION |
| vBSP-2 | 58.4% | 65.0% |
| vBSP-3 | 52.3% | 63.9% |
| vBSP-4 | 57.8% | 67.8% |
| vBSP-5x | 42.5% | 40.1% |
| vBSP-6x | 34.2% | 46.5% |

Thus, there is provided vaccine bacteria for vaccination which carry BSP fragments (vBSP-2, vBSP-3 or vBSP-4) or a multimer of the BSP tumor epitope in high amounts anchored to their surface, and which therefore trigger an immune reaction against BSP.

Example 8

Therapeutic Activity

In order to obtain a selection for the antigens or the antibodies which react as well with BSP which is in a complex with factor H, factor H or BSP isolated from bones or recombinant BSP was covalently conjugated with cyanogen bromide-activated Sepharose 4B and than a sufficient amount of BSP and factor H, respectively, applied on the column and bound so that all the ligands in the matrix were complexed to a partner. Then, the IgG fraction from serum of immunized animals was given on that affinity column and the antibody fraction obtained which had specifically bound to the free epitope in the complex of BSP and factor H. These experiments showed that particularly the 5-fold multimer vBSP5x of the eBSP epitope on vaccine bacteria elicited in rabbit extremely high antibody titers where the so produced antibodies bound to human BSP when in complex with complement factor H (CFH). These antibodies are being tested for their therapeutic activity in animal trials (nude rats with human osteotropic tumor cells) as described in WO 2002/100899.

BSP vaccine bacteria were produced with the clone pIUSind-mBSP5x for the immunization of rabbits. The plasmid pIUSind-mBSP5x was transformed in *Listeria* cells. The successful transformation was verified by preparing the plasmid DNAs from transformed *Listeria* clones and restriction analysis of the plasmid DNAs. *Listeria* pIUSind-mBSP5x bacteria were grown in a 5 ml culture in a suitable medium. The anchoring of the tumor epitopes took place during cultivation of the bacteria. The BSP vaccine bacteria were collected by centrifugation and deactivated by the adding of formaldehyde (up to 1% final concentration) over 24 h at room temperature. The quality of the BSP vaccine bacteria was assured by characterization of the deactivated vaccine bacteria in a flow through cytometer. The measurement of the deactivated BSP vaccine bacteria in FACS showed that the deactivation of the vaccine bacteria had no negative impact on the anchoring of the BSP tumor epitopes on the *Listeria*. *Listeria* pIUSind-mBSP5x and *Listeria* pIEx-A-vBSP3 (DSM 18306 and DSM 18306) have been deposited at the DSMZ (German National Resource Centre für Biological Material, Braunschweig) as examples.

The shuttle vector was transformed into weakly pathogenic Gram-positive *Listeria*. In the case of *L. monocytogenes*, the path into the cell of humans or animals is well defined. Factors such as PrfA (positive regulator of virulence), ActA (actin nucleating protein), PlcA (phosphatidylinositol-specific phospholipase), PlcB (phosphatidyl-choline-specific phospholipase), Hly (Listeriolysin), Mpl (metalloprotease) are required for the full pathogenicity of the *Listeria*, and may be specifically switched off for a reduction of the pathogenicity. The specificity between pathogen and host cell is imparted, among others, by internalins InlA and InlB. *L. monocytogeneses* may infect endothelium cells, epithelium cells, fibroblasts and hepatocytes as well as neutrophilic granulocytes, macrophages, lymphocytes and other white blood cells. After adhesion to the cell surface, *L. monocytogenes* is introduced into the cells by endocytosis. With the support of Listeriolysin (Hly), it then destroys the endosome membrane, is released into the cytosol of the host cell, proliferates there while producing the cloned fragment and other proteins, and finally infests neighboring cells. In this process, the transgenic hBSP peptide and the cloned antigenic determinant, respectively is posttranslationally modified (O- and N-glycosylated, sulphated, phosphorylated etc.) by the host cell as well as secreted and coupled onto the *Listeria* bacteria. It may then elicit an autoimmune reaction against BSP, and especially against certain fragments or epitopes of human BSP, including potential post-translational modifications. If the carrier bacteria were grown in an artificial environment and deactivated before immunization, for example by treatment with formaldehyde or addition of an antibiotic, the antigenic determinant expressed by the carrier bacterium was present on the surface of the carrier bacteria. In that case, the recombinant immune tag does not possess any post-translational modifications.

SUMMARY

The invention provides a pharmaceutical composition for the production of antibodies against human bone sialoprotein (hBSP), which binds specific epitopes on human BSP from tumor cells. The pharmaceutical composition was particular optimized for the induction of antibodies, which recognize tumorgenic hBSP in serum even when in a complex with complement factor H. Further, the invention includes microorganisms with a vector system for the induction of a specific somatic transgenicity in a host, especially in a human patient. The inventive composition particularly includes a vaccine for the induction of antibodies against bone proteins, which are produced by osteotropic tumor cells and needed for metastases into bones. The fact that proliferating tumor cells can no longer properly post-translationally process these originally strongly glycosylated proteins is indirectly exploited and used for the production of endogenous antibodies against tumorgenic proteins, which themselves are endogenous. Further, a method for vaccination and treatment of osteotropic tumors is provided which includes the use of the above methods, vaccines and active substances.

The invention claimed is:

1. A therapeutic composition for treatment of bone tumors and inhibition or treatment of metastases that preferentially settle in bone tissue comprising dead or weakly pathogenic micro-organisms into which has been introduced at least one gene encoding a peptidic antigen of a human bone sialoprotein and which express said peptidic antigen anchored on their cell surfaces so that the surface anchored antigen presents an antigenic determinant that differs from the corresponding determinant of the endogenous human bone sialoprotein of normal osteoblasts so that an immune reaction against the antigen determinant presented by the anchored peptidic antigen is induced after administration of the therapeutic composition.

2. The therapeutic composition of claim 1, wherein the expressed and surface-anchored antigenic determinant possesses structural features of a bone sialoprotein that is expressed by osteotropic cells of a primary tumor.

3. The therapeutic composition of claim 1, wherein the micro-organism is chosen from bacteria, viruses and pseudomonads.

4. The therapeutic composition of claim 1, wherein the micro-organism is a Gram-positive bacterium.

5. The therapeutic composition of claim 4, wherein the micro-organism is of the genus *Listeria*.

6. The therapeutic composition of claim 3, wherein the bacterium is one selected from the group of genera consisting of *Aeromonas, Bartonella, Bruceila, Bacilli, Bacillus subtilis, Lactobacilli, Pseudomonades, Staphylococci, Yersinia, Campylobacter, Clostridia, Enterobacteriaceae, Legionella, Mycobacterium, Rhenibacterium, Rhodococcus, Escherichia, Shigella,* and *Salmonella,* or bacteria that are viable in a eukaryotic host organism.

7. The therapeutic composition of claim 1 wherein the microorganism carries on its surface an antigenic determinant of an underglycosylated human bone sialoprotein.

8. The therapeutic composition of claim 1, wherein the expressed and surface-anchored antigenic determinant comprises an epitope of human bone sialoprotein from tumor cells which is free for specific binding by an antibody when the bone sialoprotein is in a complex with complement factor H.

9. The therapeutic composition of claim 1, wherein the expressed and surface-anchored antigenic determinant of bone sialoprotein comprises one or more copies of at least one of the following amino acid sequences:

| | |
|---|---|
| YTGLAAIQLPKKAGD | SEQ. ID NO. 5 |
| TGLAA | SEQ. ID NO. 3 |
| YTGLAA | SEQ. ID NO. 4 |
| YESENGEPRGDNYRAYED | SEQ. ID NO. 6 |
| LKRFPVQGG | SEQ. ID NO. 7 |
| EDATPGTGYTGLAAIQLPKKAG | SEQ. ID NO. 10. |

10. The therapeutic composition of claim 1, comprising as an active ingredient a protein comprising an antigenic determinant that is specifically present on bone sialoprotein from tumor cells.

11. The therapeutic composition of claim 10, wherein the active ingredient comprises an antigenic determinant of the bone sialoprotein in at least two or more copies.

12. The therapeutic composition of claim 10, wherein the protein with the antigenic determinant from bone sialoprotein is coupled to beta-alanine.

13. The therapeutic composition of claim 1, which is formulated as a vaccine.

14. A method of treatment of bone tumors and inhibition and treatment of metastatic tumor cells that preferentially settle into bone tissue comprising administering the composition of claim 1 to a subject to produce an immune reaction against said bone matrix proteins and tumor cells expressing said bone matrix proteins.

15. The method of claim 14, wherein the tumor cells are from tumors selected from the group consisting of tumors of the prostate, breast, lung, kidney, thyroid, circulatory system, lymphoid system, cardio-vascular system, neurological system, respiratory tract, digestive tract, endocrine system, skin, adnexa, musculoskeletal system and the urogenital system.

16. The therapeutic composition of claim 9, wherein the micro-organism is of the genus *Listeria*.

* * * * *

SEQUENCE LISTING

<160> NUMBER OF SEQ ID NOS: 16

<210> SEQ ID NO 1
<211> LENGTH: 15
<212> TYPE: PRT
<213> ORGANISM: Homo sapiens

<400> SEQUENCE: 1

Tyr Thr Gly Leu Ala Ala Ile Gln Leu Pro Lys Lys Ala Gly Asp
 1               5                  10                  15

<210> SEQ ID NO 2
<211> LENGTH: 297
<212> TYPE: PRT
<213> ORGANISM: Homo sapiens

<400> SEQUENCE: 2

Phe Ser Met Lys Asn Leu His Arg Arg Val Lys Ile Glu Asp Ser Glu
 1               5                  10                  15

Glu Asn Gly Val Phe Lys Tyr Arg Pro Arg Tyr Tyr Leu Tyr Lys His
                20                  25                  30

Ala Tyr Phe Tyr Pro His Leu Lys Arg Phe Pro Val Gln Gly Ser Ser
            35                  40                  45

Asp Ser Ser Glu Glu Asn Gly Asp Asp Ser Ser Glu Glu Glu Glu Glu
        50                  55                  60

Glu Glu Glu Thr Ser Asn Glu Gly Glu Asn Asn Glu Glu Ser Asn Glu
65                  70                  75                  80

Asp Glu Asp Ser Glu Ala Glu Asn Thr Thr Leu Ser Ala Thr Thr Leu
                85                  90                  95

Gly Tyr Gly Glu Asp Ala Thr Pro Gly Thr Gly Tyr Thr Gly Leu Ala
            100                 105                 110

Ala Ile Gln Leu Pro Lys Lys Ala Gly Asp Ile Thr Asn Lys Ala Thr
        115                 120                 125

Lys Glu Lys Glu Ser Asp Glu Glu Glu Glu Glu Glu Glu Glu Gly Asn
130                 135                 140

Glu Asn Glu Glu Ser Glu Ala Glu Val Asp Glu Asn Glu Gln Gly Ile
145                 150                 155                 160

Asn Gly Thr Ser Thr Asn Ser Thr Glu Ala Glu Asn Gly Asn Gly Ser
                165                 170                 175

Ser Gly Val Asp Asn Gly Glu Glu Gly Glu Glu Ser Val Thr Gly
            180                 185                 190

Ala Asn Ala Glu Gly Thr Thr Glu Thr Gly Gly Gln Gly Lys Gly Thr
        195                 200                 205

Ser Lys Thr Thr Thr Ser Pro Asn Gly Gly Phe Glu Pro Thr Thr Pro
210                 215                 220

Pro Gln Val Tyr Arg Thr Thr Ser Pro Pro Phe Gly Lys Thr Thr Thr
225                 230                 235                 240

Val Glu Tyr Glu Gly Glu Tyr Glu Tyr Thr Tyr Asp Asn Gly Tyr Glu
                245                 250                 255

Ile Tyr Glu Ser Glu Asn Gly Glu Pro Arg Gly Asp Asn Tyr Arg Ala
            260                 265                 270

Tyr Glu Gly Glu Tyr Ser Tyr Phe Lys Gly Gln Gly Tyr Asp Gly Tyr
        275                 280                 285

Asp Gly Gln Asn Tyr Tyr His His Gln
    290                 295

```
<210> SEQ ID NO 3
<211> LENGTH: 5
<212> TYPE: PRT
<213> ORGANISM: Homo sapiens

<400> SEQUENCE: 3

Thr Gly Leu Ala Ala
1               5

<210> SEQ ID NO 4
<211> LENGTH: 6
<212> TYPE: PRT
<213> ORGANISM: Homo sapiens

<400> SEQUENCE: 4

Tyr Thr Gly Leu Ala Ala
1               5

<210> SEQ ID NO 5
<211> LENGTH: 15
<212> TYPE: PRT
<213> ORGANISM: Homo sapiens

<400> SEQUENCE: 5

Tyr Thr Gly Leu Ala Ala Ile Gln Leu Pro Lys Lys Ala Gly Asp
1               5                   10                  15

<210> SEQ ID NO 6
<211> LENGTH: 18
<212> TYPE: PRT
<213> ORGANISM: Homo sapiens

<400> SEQUENCE: 6

Tyr Glu Ser Glu Asn Gly Glu Pro Arg Gly Asp Asn Tyr Arg Ala Tyr
1               5                   10                  15

Glu Asp

<210> SEQ ID NO 7
<211> LENGTH: 9
<212> TYPE: PRT
<213> ORGANISM: Homo sapiens

<400> SEQUENCE: 7

Leu Lys Arg Phe Pro Val Gln Gly Gly
1               5

<210> SEQ ID NO 8
<211> LENGTH: 7
<212> TYPE: PRT
<213> ORGANISM: Homo sapiens

<400> SEQUENCE: 8

Ser Gly Gly Gly Gly Ser Ala
1               5

<210> SEQ ID NO 9
<211> LENGTH: 7
<212> TYPE: PRT
<213> ORGANISM: Homo sapiens

<400> SEQUENCE: 9

Asp Ala Thr Pro Gly Thr Gly
1               5
```

```
<210> SEQ ID NO 10
<211> LENGTH: 22
<212> TYPE: PRT
<213> ORGANISM: Homo sapiens

<400> SEQUENCE: 10

Glu Asp Ala Thr Pro Gly Thr Gly Tyr Thr Gly Leu Ala Ala Ile Gln
1               5                   10                  15

Leu Pro Lys Lys Ala Gly
            20

<210> SEQ ID NO 11
<211> LENGTH: 12
<212> TYPE: PRT
<213> ORGANISM: Homo sapiens

<400> SEQUENCE: 11

Leu Gly Tyr Gly Glu Asp Ala Thr Pro Gly Thr Gly
1               5                   10

<210> SEQ ID NO 12
<211> LENGTH: 12
<212> TYPE: PRT
<213> ORGANISM: Homo sapiens

<400> SEQUENCE: 12

Glu Thr Gly Gly Gln Gly Lys Gly Thr Ser Lys Thr
1               5                   10

<210> SEQ ID NO 13
<211> LENGTH: 12
<212> TYPE: PRT
<213> ORGANISM: Homo sapiens

<400> SEQUENCE: 13

Phe Lys Gly Gln Gly Tyr Asp Gly Tyr Asp Gly Gln
1               5                   10

<210> SEQ ID NO 14
<211> LENGTH: 15
<212> TYPE: PRT
<213> ORGANISM: Homo sapiens

<400> SEQUENCE: 14

Ile Gln Leu Pro Lys Lys Ala Gly Asp Ile Thr Asn Lys Ala Thr
1               5                   10                  15

<210> SEQ ID NO 15
<211> LENGTH: 17
<212> TYPE: PRT
<213> ORGANISM: homo sapiens

<400> SEQUENCE: 15

Gly Asp Ile Thr Asn Lys Ala Thr Lys Glu Lys Glu Lys Glu Ser Asp
1               5                   10                  15

Glu

<210> SEQ ID NO 16
<211> LENGTH: 38
<212> TYPE: PRT
<213> ORGANISM: Homo sapiens

<400> SEQUENCE: 16

Ser Glu Asn Gly Glu Pro Arg Gly Asp Asn Tyr Arg Ala Tyr Glu Asp
1               5                   10                  15
```

```
Glu Tyr Ser Tyr Phe Lys Gly Gln Gly Tyr Asp Gly Tyr Asp Gly Gln
            20                  25                  30

Asn Tyr Tyr His His Gln
        35
```